US00PP08750P

United States Patent [19]

Hanes

[11] Patent Number: Plant 8,750

[45] Date of Patent: May 24, 1994

[54] GERANIUM NAMED AMERICANA VIOLET

[75] Inventor: Mitchell Hanes, Morgan Hill, Calif.

[73] Assignee: Goldsmith Seeds, Inc., Gilroy, Calif.

[21] Appl. No.: 50,528

[22] Filed: Apr. 20, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new geranium cultivar particularly distinguished by its semi-double large magenta violet flowers. The plant itself has vigorous growth, growing to a height of 7–11 cm. as a 4 inch potted plant.

1 Drawing Sheet

BACKGROUND OF THE NEW PLANT

The present invention comprises a new and distinct cultivar of geranium, botanically known as *Pelargonium hortorum* Bailey. The new cultivar is propagated from a seedling resulting from the cross of a violet, single flower, unreleased proprietary, seed parent known as 423-6 and a pollen parent Americana Cherry Rose (U.S. Plant Pat. No. 7,937). Americana Cherry Rose was chosen as one parent to contribute good vigor and habit, along with a semidouble flower, to the hybrid.

This new plant is a product of a planned breeding program intended to create new geranium cultivars with magneta violet colored semi-double flowers, green foliage, with vigorous growth and superior cutting productivity.

The new cultivar was created in 1990 in Gilroy, Calif., and has been repeatedly asexually reproduced by cuttings in Gilroy, Calif., and Guatemala over a three year period. It has also been trailed at Okemos, Mich. It has been found to retain its distinctive characteristics through successive propagations; and this novelty appears to be firmly fixed.

DESCRIPTION OF THE DRAWING

This new geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics was collected from asexual reproductions carried out in Gilroy, Calif. The plant history was taken on 10 week old plants, blossomed under natural light in a greenhouse. Color readings were taken in the greenhouse on Mar. 15, 1993 under ambient light. Color references are primarily to the R.H.S. Colour Chart of the Royal Horticultural Society of London.

THE PLANT

Classification:

*Botanical.*—*Pelargonium hortorum* Bailey.

*Commercial.*—Zonal geranium.

Form: Upright and somewhat open as a young plant.

Height: 7 to 11 cm. as a 4 inch potted plant, excluding blooms.

Growth: Strong.

Internode: Approximately 1.2–1.8 cm.

Strength: The plant is earlier and more compact than other varieties in the color class. The plant performs very well after shipping as a rooted or unrooted cutting.

Foliage: Abundant quantity.

*Leaves.*—Normal, inconspicuous zonation.

*Size.*—Diameter about 9 cm.

*Shape.*—Cordate, with rounded apex, to reniform with occasional upfolding between veins.

*Margin.*—Irregularly crenate.

*Texture.*—Leathery and pubescent on both surfaces, especially along veins.

*Ribs and veins.*—Distinctly palmate, 4.5 to 6.0 cm. long.

*Color.*—Upper side: Green with lighter green zonation. Under side: Lighter green color. Ribs and veins not prominently different from the upper surface.

Petioles: About 4.5 to 6.0 cm. in length.

THE BUD

Size:

*Diameter.*—About 5 mm.

*Length.*—About 2.2 to 2.7 cm. at the time of bud opening.

Shape: Pointed ovoid.

Color: Of petals when sepals first divide, RHS 67-A.

Sepals: Five in number, flat behind petals, pointed linear lanceolate, RHS 143-C in an open flower.

THE FLOWER

Blooming habit: Continuous throughout the year when grown in a frost free environment.

Size: Approximately 5.0 cm in diameter, 1.5 cm. deep, irregularly radially symmetrical.

Form: Cup-shaped when bloom first opens, later flattening to shallow cup shape with maturity.

Petals: Five imbricate outer petals, 2.5–2.8 cm. wide and approximately 2.6 cm. long. Five to six inner smaller petaloids of varying shape. Both the outer petals and inner petaloids are magenta violet, RHS 66-A. The base of the two upper outside petals each have an orange splotch. The veins are not significantly darker than the interveinal regions. Color changing little with age. Petals and petaloids are soft and satiny.

Pedicel: Approximately 2.5 cm. in length.
Persistence: Nonshattering flower.

INFLORESCENCE

Type: An umbel composed of approximately 25–30 flowers, erect or laterally ascending with a maximum diameter of about 13 cm. On a 12 week old plant, in a 6" pot, typically there will be 2–3 umbels.

Peduncle: Approximately 7–10 cm. in length, green in color with slight reddish speckling on the side exposed to the sun.

REPRODUCTIVE ORGANS

Stamens: Normal for species.

*Anthers.*—Six to eight positioned below the mature stigma, dull red prior to anthesis.

*Filaments.*—White near base and mid-length, graduating to dull red near the anther.

*Pollen.*—Orange in color.

Pistil: Normal for species.

*Number.*—One.

*Length.*—Approximately 4 mm.

Stigma: Five linear lobes of near equal length, curling back toward the ovary, purplish-red in color.

*Style.*—Normal.

*Length.*—About 3 mm.

*Color.*—Purplish-red.

Ovaries: At anthesis, densely pubescent with white hairs, oblong. Green drying to a light brown at maturity.

Fruit: Partially fertile. Infrequent seed set that does not reduce the continuous flowering nature of the plant.

I claim:

1. A new and distinct geranium cultivar substantially as herein shown and described, characterized by its magenta violet colored, semi-double flowers on large umbels, green foliage without a light zonation; the plant being fast rooting and having a vigorous upright growth habit.

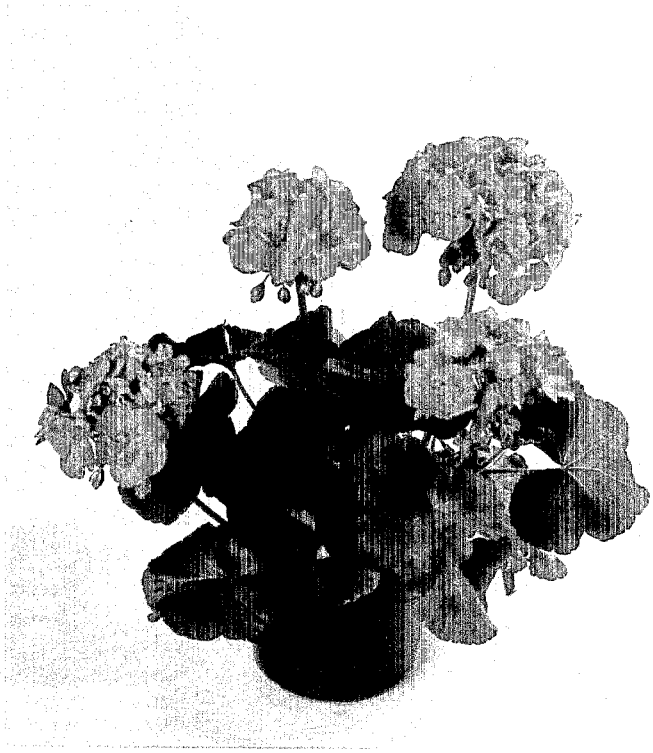

* * * * *